US007877213B2

(12) United States Patent
Ghosh et al.

(10) Patent No.: US 7,877,213 B2
(45) Date of Patent: Jan. 25, 2011

(54) SYSTEM AND METHODS FOR AUTOMATED PROCESSING OF MULTIPLE CHEMICAL ARRAYS

(75) Inventors: Jayati Ghosh, Sunnyvale, CA (US); Charles D. Troup, Livermore, CA (US); Xiangyang Zhou, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 931 days.

(21) Appl. No.: 11/233,560

(22) Filed: Sep. 22, 2005

(65) Prior Publication Data

US 2007/0174007 A1 Jul. 26, 2007

Related U.S. Application Data

(60) Provisional application No. 60/613,076, filed on Sep. 23, 2004.

(51) Int. Cl.
G01N 33/48 (2006.01)
(52) U.S. Cl. ....................................................... 702/19
(58) Field of Classification Search ................... 702/19
See application file for complete search history.

(56) References Cited

U.S. PATENT DOCUMENTS

| | | | |
|---|---|---|---|
| 5,001,766 A | 3/1991 | Baird | |
| 5,487,115 A | 1/1996 | Surka | |
| 5,627,912 A | 5/1997 | Matsumoto | |
| 5,837,475 A | 11/1998 | Dorsel et al. | |
| 5,916,747 A | 6/1999 | Cilchrist et al. | |
| 5,948,902 A | 9/1999 | Honkanen et al. | |
| 6,171,797 B1 | 1/2001 | Perbost | |
| 6,180,351 B1 | 1/2001 | Cattell | |
| 6,221,583 B1 | 4/2001 | Kayyem et al. | |
| 6,222,664 B1 | 4/2001 | Dorsel et al. | |
| 6,232,072 B1 | 5/2001 | Fisher | |
| 6,242,266 B1 | 6/2001 | Schleifer et al. | |
| 6,251,685 B1 | 6/2001 | Dorsel et al. | |
| 6,320,196 B1 | 11/2001 | Dorsel et al. | |
| 6,323,043 B1 | 11/2001 | Caren et al. | |
| 6,349,144 B1 | 2/2002 | Shams | |
| 6,355,921 B1 | 3/2002 | Staton et al. | |
| 6,362,832 B1 | 3/2002 | Stephan et al. | |
| 6,371,370 B2 | 4/2002 | Sadler et al. | |
| 6,406,849 B1 | 6/2002 | Dorsel et al. | |
| 6,486,457 B1 | 11/2002 | Dorsel et al. | |
| 6,498,863 B1 | 12/2002 | Gaidoukevitch et al. | |
| 6,518,556 B2 | 2/2003 | Staton et al. | |
| 6,571,005 B1 | 5/2003 | Li et al. | |
| 6,591,196 B1 | 7/2003 | Kakhini et al. | |
| 6,756,202 B2 | 6/2004 | Dorsel et al. | |
| 2002/0102558 A1 | 8/2002 | Cattell | |
| 2003/0143551 A1 | 7/2003 | Cattell et al. | |
| 2003/0160183 A1 | 8/2003 | Dorsel et al. | |
| 2004/0094626 A1 | 5/2004 | Sillman et al. | |
| 2004/0152082 A1 | 8/2004 | Troup et al. | |

FOREIGN PATENT DOCUMENTS

| | | |
|---|---|---|
| EP | 0 380 659 A1 | 8/1990 |
| WO | WO 99/08233 | 2/1999 |
| WO | WO 01/06395 | 1/2001 |

OTHER PUBLICATIONS

Glasbey et al., "Combinatorial Image Analysis of DNA Features," Bioinformatics (Jan. 22, 2003) vol. 19, No. 2, pp. 194-203.*
Cheung, R.C.Y. et al., "Analysis of Gene Microarray Images,"1999, pp. 627-632.
Douglas E. Bassett Jr., et al., "Gene expression informatics—it's all in your mine," Nature Genetics Supplement, vol. 21, Jan. 1999, pp. 51-55.
Kuklin A., et al., "High throughput screening of gene expression signatures," Genetica, vol. 108, 2000, pp. 41-46.
Michael Eisen., et al., "ScanAlyze User Manual," Jul. 14, 1999, pp. 1-22.
GenePix Pro 4.1, Axon Instruments, http://www.axon.com/GN_GenePixSofgtware.html, pp. 1-10, downloaded May 1, 2003.
GenePix Pro 6.0 Microarry Image Analysis. Axon Instruments, http://www.axon.com/GN_GenePixSoftware.html, pp. 1-9, downloaded Sep. 20, 2004.
Welcome to BioDiscovery. http://www.biodiscovery.com/imagene.asp, pp. 1-2, 2004.
Jesus Angula and Jean Serra, Automatic analysis of DNA microarray images using mathematical morphology, 2003, Bioinformatics vol. 19 No. 5, pp. 553-562.

* cited by examiner

*Primary Examiner*—Jerry Lin

(57) ABSTRACT

A system and method of operating a data processing system to provide feature extraction from an image obtained from a plurality of chemical arrays is disclosed. The method includes bifurcating processing of the image by performing image processing and post-processing. The image processing includes processing parts of the image, each part corresponding to a different one of the arrays, in an automated batch process, to produce image-processed outputs that are different from the image and contain information extracted from the image. The post-processing includes processing the image-processed outputs according to different post-processing protocols with respect to different ones of those parts of the image corresponding to at least two of the arrays, to produce post-processed outputs. The method includes outputting at least one of the image-processed outputs and/or at least one of the post-processed outputs.

24 Claims, 10 Drawing Sheets
(2 of 10 Drawing Sheet(s) Filed in Color)

SYSTEM AND METHODS FOR AUTOMATED PROCESSING OF MULTIPLE CHEMICAL ARRAYS

CROSS-REFERENCE

This application claims the benefit of U.S. Provisional Application No. 60/613,076, filed Sep. 23, 2004, which application is incorporated herein, in its entirety, by reference thereto.

BACKGROUND OF THE INVENTION

Array assays between surface bound binding agents or probes and target molecules in solution are used to detect the presence of particular biopolymers. The surface-bound probes may be oligonucleotides, peptides, polypeptides, proteins, antibodies or other molecules capable of binding with target molecules in solution. Such binding interactions are the basis for many of the methods and devices used in a variety of different fields, e.g., genomics (in sequencing by hybridization, SNP detection, differential gene expression analysis, comparative genomic hybridization, identification of novel genes, gene mapping, finger printing, etc.) and proteomics.

One typical array assay method involves biopolymeric probes immobilized in an array on a substrate such as a glass substrate or the like. A solution containing analytes that bind with the attached probes is placed in contact with the array substrate, covered with another substrate such as a coverslip or the like to form an assay area and placed in an environmentally controlled chamber such as an incubator or the like. Usually, the targets in the solution bind to the complementary probes on the substrate to form a binding complex. The pattern of binding by target molecules to biopolymer probe features or spots on the substrate produces a pattern on the surface of the substrate and provides desired information about the sample. In most instances, the target molecules are labeled with a detectable tag such as a fluorescent tag or chemiluminescent tag. The resultant binding interaction or complexes of binding pairs are then detected and read or interrogated, for example by optical means, although other methods may also be used. For example, laser light may be used to excite fluorescent tags, generating a signal only in those spots on the biochip (substrate) that have a target molecule and thus a fluorescent tag bound to a probe molecule. This pattern may then be digitally scanned for computer analysis.

As such, optical scanners play an important role in many array based applications. Optical scanners act like a large field fluorescence microscope in which the fluorescent pattern caused by binding of labeled molecules on the array surface is scanned. In this way, a laser induced fluorescence scanner provides for analyzing large numbers of different target molecules of interest, e.g., genes/mutations/alleles, in a biological sample.

Scanning equipment used for the evaluation of arrays typically includes a scanning fluorometer. A number of different types of such devices are commercially available from different sources, such as Perkin-Elmer, Agilent Technologies, Inc., Axon Instruments, and others. In such devices, a laser light source generates a collimated beam. The collimated beam is focused on the array and sequentially illuminates small surface regions of known location on an array substrate. The resulting fluorescence signals from the surface regions are collected either confocally (employing the same lens to focus the laser light onto the array) or off-axis (using a separate lens positioned to one side of the lens used to focus the laser onto the array). The collected signals are then transmitted through appropriate spectral filters, to an optical detector. A recording device, such as a computer memory, records the detected signals and builds up a raster scan file of intensities as a function of position, or time as it relates to the position.

Analysis of the data (the stored file) may involve collection, reconstruction of the image, feature extraction from the image and quantification of the features extracted for use in comparison and interpretation of the data. Where large numbers of array files are to be analyzed, the various arrays from which the files were generated upon scanning may vary from each other with respect to a number of different characteristics, including the types of probes used (e.g., polypeptide or nucleic acid), the number of probes (features) deposited, the size, shape, density and position of the array of probes on the substrate, the geometry of the array, whether or not multiple arrays or subarrays are included on a single slide and thus in a single, stored file resultant from a scan of that slide, etc.

Previous automated solutions for feature extraction processing of images produced by scanning or one of the alternative techniques mentioned above do not have the capability of splitting image processing or feature extraction pre-processing and post-processing steps or procedures for analyzing the images. Thus, for processing images that contain multiple arrays or subarrays, for example, feature extraction processing, when using previous solutions, requires first splitting, cropping or dividing such images into component sub-images that each only contain a single array or subarray, prior to feature extracting the sub-images. This requires a user to save multiple files for a single image, one for each array or subarray.

Also, previous solutions typically do not have the ability to perform inter-array analysis, which refers to comparing post-processing results or outputs (i.e., processed outputs) of features located on different arrays. The different arrays on which the features are located may be on the same substrate or on different substrates. Inter-array analysis capabilities are important, particularly for one-color slides, substrates or arrays, or for finding a set of dye normalization probes from combined data analysis of multiple arrays, for example. Another important use for inter-array analysis is for performing a gene expression, proteomics, or other chemical or biochemical experiment where the content of the experiment extends over multiple arrays.

There remain continuing needs for improved solutions for efficiently imaging and analyzing array images in a manner where post processing of multiple arrays can be done in a combined fashion. Further, there are continuing needs for improved solutions for inter-array image processing while providing the ability to post-process separately.

SUMMARY OF THE INVENTION

Methods, systems and computer-readable media for bifurcating automated feature extraction processing of chemical arrays are provided to image-process a plurality of the arrays sequentially, and post-process outputs resulting from the image processing of at least two of the plurality of the arrays in an automated batch process to obtain processed outputs.

Methods, systems and computer readable media are provided for bifurcating automated feature extraction processing for chemical arrays, to include image-processing a plurality of the arrays in an automated batch process; and post-processing outputs resulting from the image processing according to different post-processing protocols with respect to at least two of the plurality of the arrays.

Methods, systems and computer readable media are provided for bifurcating automated feature extraction processing of chemical arrays, to include image processing an array; and post-processing an output of the image processing in an automated batch process, including assigning at least two different post-processing protocols, each to the output, and outputting processed outputs for each processing protocol.

Methods, systems and computer readable media are provided for performing inter-array analysis, including: image processing a first array with a first image processing protocol to obtain a first output; image processing a second array with a second image processing protocol to obtain a second output; and post-processing the first and second outputs of the image processing of the first and second arrays in an automated batch process to obtain processed outputs.

Methods, systems and computer readable media for feature extraction processing of multiple arrays contained on a single substrate are provided, to include image processing the multiple arrays in an automated batch process; and post-processing outputs of individual arrays, resulting from the image processing of the multiple arrays, according to at least one post-processing protocol.

These and other advantages and features of the invention will become apparent to those persons skilled in the art upon reading the details of the methods, systems and computer readable media as more fully described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
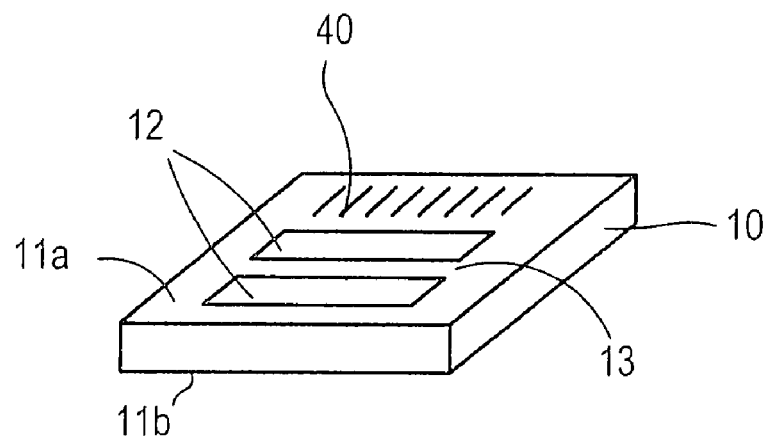
FIG. 1 illustrates a substrate carrying multiple arrays, such as may be processed according to the present invention.

Before the present methods, systems and computer readable media are described, it is to be understood that this invention is not limited to particular software, hardware, process steps or substrates described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a probe" includes a plurality of such probes and reference to "the array" includes reference to one or more arrays and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

A "microarray", "bioarray" or "array", unless a contrary intention appears, includes any one-, two- or three-dimensional arrangement of addressable regions bearing a particular chemical moiety or moieties associated with that region. A microarray is "addressable" in that it has multiple regions of moieties such that a region at a particular predetermined location on the microarray will detect a particular target or class of targets (although a feature may incidentally detect non-targets of that feature). Array features are typically, but need not be, separated by intervening spaces. In the case of an array, the "target" will be referenced as a moiety in a mobile phase, to be detected by probes, which are bound to the substrate at the various regions. However, either of the "target" or "target probes" may be the one, which is to be evaluated by the other.

Methods to fabricate arrays are described in detail in U.S. Pat. Nos. 6,242,266; 6,232,072; 6,180,351; 6,171,797 and 6,323,043. As already mentioned, these references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods as described in those patents.

Following receipt by a user, an array will typically be exposed to a sample and then read. Reading of an array may be accomplished by illuminating the array and reading the location and intensity of resulting fluorescence at multiple regions on each feature of the array. For example, a scanner may be used for this purpose is the AGILENT MICROARRAY SCANNER manufactured by Agilent Technologies, Palo, Alto, Calif. or other similar scanner. Other suitable apparatus and methods are described in U.S. Pat. Nos. 6,518,556; 6,486,457; 6,406,849; 6,371,370; 6,355,921; 6,320,196; 6,251,685 and 6,222,664. Scanning typically produces a scanned image of the array which may be directly inputted to a feature extraction system for direct processing and/or saved in a computer storage device for subsequent processing. However, arrays may be read by any other methods or apparatus than the foregoing, other reading methods including other optical techniques, such as a CCD, for example, or electrical techniques (where each feature is provided with an electrode to detect bonding at that feature in a manner disclosed in U.S. Pat. Nos. 6,251,685, 6,221,583 and elsewhere).

A "design file" is typically provided by an array manufacturer and is a file that embodies all the information that the array designer from the array manufacturer considered to be pertinent to array interpretation. For example, Agilent Technologies supplies its array users with a design file written in the XML language that describes the geometry as well as the biological content of a particular array.

A "grid template" or "design pattern" is a description of relative placement of features, with annotation, that has not been placed on a specific image. A grid template or design pattern can be generated from parsing a design file and can be saved/stored on a computer storage device. A grid template has basic grid information from the design file that it was generated from, which information may include, for example, the number of rows in the array from which the grid template was generated, the number of columns in the array from which the grid template was generated, column spacings, subgrid row and column numbers, if applicable, spacings between subgrids, number of arrays/hybridizations on a slide, etc. An alternative way of creating a grid template is by using an interactive grid mode provided by the system, which also provides the ability to add further information, for example, such as subgrid relative spacings, rotation and skew information, etc.

A "grid file" contains even more information than a "grid template", and is individualized to a particular image or group of images. A grid file can be more useful than a grid template in the context of images with feature locations that are not characterized sufficiently by a more general grid template description. A grid file may be automatically generated by placing a grid template on the corresponding image, and/or with manual input/assistance from a user. One main difference between a grid template and a grid file is that the grid file specifies an absolute origin of a main grid and rotation and skew information characterizing the same. The information provided by these additional specifications can be useful for a group of slides that have been similarly printed with at least one characteristic that is out of the ordinary or not normal, for example. In comparison when a grid template is placed or overlaid on a particular microarray image, a placing algorithm of the system finds the origin of the main grid of the image and also its rotation and skew. A grid file may contain subgrid relative positions and their rotations and skews. The grid file may even contain the individual spot centroids and even spot/feature sizes.

A "history" or "project history" file is a file that specifies all the settings used for a project that has been run, e.g., extraction names, images, grid templates protocols, etc. The history file may be automatically saved by the system and is not modifiable. The history file can be employed by a user to easily track the settings of a previous batch run, and to run the same project again, if desired, or to start with the project settings and modify them somewhat through user input.

"Image processing" or a "pre-processing" phase of feature extraction processing refers to processing of an electronic image file representing a slide containing at least one array, which is typically, but not necessarily in TIFF (Tagged Image File Format) format, wherein processing is carried out to find a grid that fits the features of the array, to find individual spot/feature centroids, spot/feature radii, etc. Image processing may even include processing signals from the located features to determine mean or median signals from each feature and/or its surrounding background region and may further include associated statistical processing. At the end of an image processing step, a user has all the information that needs to be gathered from the image.

"Post processing" or "post processing/data analysis", sometimes just referred to as "data analysis" refers to processing signals from the located features, obtained from the image processing, to extract more information about each feature. Post processing may include but is not limited to various background level subtraction algorithms, dye normalization processing, finding ratios, and other processes known in the art. Outputs from post processing, or "processed outputs" include, but are not limited to: feature intensity signals after background subtraction of the inputted signals, feature intensity signals after dye normalization of the inputted signals, expression ratios of feature intensity signals, with or without background subtraction and/or dye normalization having been applied, feature intensity signals after background subtraction and dye normalization of the inputted signals, etc.

A "protocol" provides feature extraction parameters for algorithms (which may include image processing algorithms and/or post processing algorithms to be performed at a later stage or even by a different application) for carrying out feature extraction and interpretation from an image that the protocol is associated with. Thus, an "image processing protocol" provides parameters for processing an inputted array image (e.g., a TIFF image), wherein such parameters may include, but are not limited to: grid finding parameters such as coordinates and layout of a grid, spot finding parameters such as deviation limit of a centroid from the grid locations, cookie size, indications of what percentage of a cookie are to be used for signal metric calculations, signal and background metrics to calculate (e.g., means signal, median signal, standard deviation, etc.), methods of outlier flagging to be used, etc. The output from image processing includes results from processing according to the image processing protocol in combination with the grid template used, and may include, but is not limited to: grid locations, feature sizes, feature centroids, mean feature signal intensity, median feature signal intensity, standard deviation of signal intensity, mean background signal, median background signal and/or standard deviation of background signal. A "post-processing protocol provides parameters for processes to be carried out during post-processing. Examples of processes that may be identified in the post-processing protocol to be carried out on an output from image processing include, but are not limited to: local background subtraction, negative control background subtraction, dye normalization, selection of a specific set of genes to be used as a dye normalization set upon which to perform dye normalization, computation of signal intensities after dye normalization and/or background subtraction, calculation of signal intensity ratios, with or without dye normalization and/or background subtraction and/or calculation of other metrics characterizing the feature signal intensity and/or background signal intensity, including population outliers, saturated features, etc. Protocols are user definable and may be saved/stored on a computer storage device, thus providing users flexibility in regard to assigning/pre-assigning protocols to specific microarrays and/or to specific types of microarrays. The system may use protocols provided by a manufacturer(s) for extracting arrays prepared according to recommended practices, as well as user-definable and savable protocols to process a single microarray or to process multiple microarrays on a global basis, leading to reduced user error. The system may maintain a plurality of protocols (in a database or other computer storage facility or device) that describe and parameterize different processes that the system may perform. The system also allows users to import and/or export a protocol to or from its database or other designated storage area.

An "extraction" refers to a unit containing information needed to perform feature extraction on a scanned image that includes one or more arrays in the image. An extraction includes an image file and, associated therewith, a grid template or grid file and protocol(s) (image and post processing).

A "feature extraction project" or "project" refers to a smart container that includes one or more extractions that may be processed automatically, one-by-one, in a batch. An extraction is the unit of work operated on by the batch processor. Each extraction includes the information that the system needs to process the slide (scanned image) associated with that extraction.

When one item is indicated as being "remote" from another, this is referenced that the two items are at least in different buildings, and may be at least one mile, ten miles, or at least one hundred miles apart.

"Communicating" information references transmitting the data representing that information as electrical signals over a suitable communication channel (for example, a private or public network).

"Forwarding" an item refers to any means of getting that item from one location to the next, whether by physically transporting that item or otherwise (where that is possible) and includes, at least in the case of data, physically transporting a medium carrying the data or communicating the data.

A "processor" references any hardware and/or software combination which will perform the functions required of it. For example, any processor herein may be a programmable digital microprocessor such as available in the form of a mainframe, server, or personal computer. Where the processor is programmable, suitable programming can be communicated from a remote location to the processor, or previously saved in a computer program product. For example, a magnetic or optical disk may carry the programming, and can be read by a suitable disk reader communicating with each processor at its corresponding station.

Reference to a singular item, includes the possibility that there are plural of the same items present.

"May" means optionally.

Methods recited herein may be carried out in any order of the recited events which is logically possible, as well as the recited order of events.

All patents and other references cited in this application, are incorporated into this application by reference except insofar as they may conflict with those of the present application (in which case the present application prevails).

Figure 2:
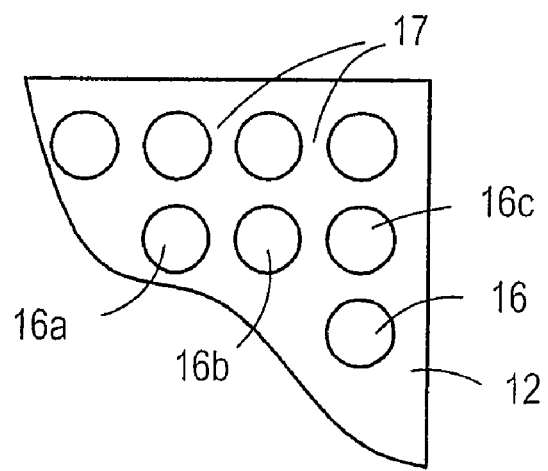
FIG. 2 is an enlarged, partial schematic view of a portion of the substrate of FIG. 1, showing ideal spots or features.

Referring first to FIGS. 1-2, typically methods and systems described herein analyze features that are originally contained on a contiguous planar substrate 10 carrying one or more arrays 12 disposed across a front surface 11a of substrate 10 and separated by inter-array areas 13 when multiple arrays are present. A back side 11b of substrate 10 typically does not carry any arrays 12. The arrays on substrate 10 can be designed for testing against any type of sample, whether a trial sample, reference sample, a combination of them, or a known mixture of polynucleotides (in which latter case the arrays may be composed of features carrying unknown sequences to be evaluated). While two arrays 12 are shown in FIG. 1, it will be understood that substrate 10 may have any number of desired arrays 12.

Arrays on any same substrate 10 may all have the same array layout, or some or all may have different array layouts. Similarly, substrate 10 may be of any shape, and any apparatus used with it adapted accordingly. Depending upon intended use, any or all of arrays 12 may be the same or different from one another and each may contain multiple spots or features 16 of biopolymers in the form of polynucleotides. A typical array may contain from more than ten, more than one hundred, more than one thousand or more than ten thousand features. All of the features 16 may be different, or some could be the same (for example, when any repeats of each feature composition are excluded the remaining features may account for at least 5%, 10%, or 20% of the total number of features).

Features 16 may be arranged in straight line rows extending left to right, such as shown in the partial view of FIG. 2, for example. In the case where arrays 12 are formed by the conventional in situ or deposition of previously obtained moieties, by depositing for each feature a droplet of reagent in each cycle such as by using a pulse jet such as an inkjet type head, interfeature areas 17 will typically be present which do not carry any polynucleotide or moieties of the array features. It will be appreciated though, that the interfeature areas 17 could be of various sizes and configurations. It will also be appreciated that there need not be any space separating arrays 12 from one another although there typically will be. Each feature carries a predetermined polynucleotide (which includes the possibility of mixtures of polynucleotides). As per usual, A, C, G, T represent the usual nucleotides. It will be understood that there may be a linker molecule (not shown) of any known types between the front surface 11a and the first nucleotide.

A substrate/array identifier 40, such as a bar code or other readable format identifier, for both arrays 12 in FIG. 1, is associated with those arrays 12 to which it corresponds, by being provided on the same substrate 10 adjacent one of the arrays 12. A separate identifier can be provided adjacent each corresponding array 12 if desired. Identifier 40 may either contain information on the layout of array 12 or be linkable to a file containing such information in a manner such as described in co-pending, commonly owned application Ser. No. 10/941,501, filed Sep. 15, 2004 and titled "Automated Feature Extraction Processes and Systems", co-pending, commonly owned application Ser. No. 10/946,142, filed Sep. 20, 2004 and titled "Automated Processing of Chemical Arrays and Systems Therefore", and further described below, or in U.S. Pat. No. 6,180,351. application Ser. No. 10/941,501, application Ser. No. 10/946,142, and U.S. Pat. No. 6,180,351 are each hereby incorporated herein, in their entireties, by reference thereto. Each identifier 40 for different arrays may be unique so that a given identifier will likely only correspond to one array 12 or to arrays 12 on the same substrate 10. This can be accomplished by making identifier 40 sufficiently long and incrementing or otherwise varying it for different arrays 12 or arrays 12 on the same substrate 10, or even by selecting it to be globally unique in a manner in which globally unique identifiers are selected as described in U.S. Pat. No. 6,180,351. However, a portion of identifier 40 may identify a type or group of arrays that have common characteristics and therefore may be at least partially processed in a similar manner, such as with the same grid template and/or the same protocol, etc.

Features 16 can have widths (that is, diameter, for a round feature 16) in the range of at least 10 μm, to no more than 1.0 cm. In embodiments where very small spot sizes or feature sizes are desired, material can be deposited according to the invention in small spots whose width is at least 1.0 μm, to no more than 1.0 mm, usually at least 5.0 μm to no more than 500 μm, and more usually at least 10 μm to no more than 200 μm. The size of features 16 can be adjusted as desired, during array fabrication. Features which are not round may have areas equivalent to the area ranges of round features 16 resulting from the foregoing diameter ranges.

For the purposes of the above description of FIGS. 1-2 and the discussions below, it will be assumed (unless the contrary is indicated) that the array being formed in any case is a polynucleotide array formed by the deposition of previously obtained polynucleotides using pulse jet deposition units. However, it will be understood that the described methods are applicable to arrays of other polymers (such as biopolymers), proteins or chemical moieties generally, whether formed by multiple cycle in situ methods using precursor units for the moieties desired at the features, or deposition of previously obtained moieties, or using other types of dispensers. Thus, in those discussions "polynucleotide", "polymer" (such as "biopolymer"). "protein" or "chemical moiety", can generally be interchanged with one another (although where specific chemistry is referenced the corresponding chemistry of an interchanged moiety should be referenced instead). It will also be understood that when methods such as an in situ fabrication method are used, additional steps may be required (such as oxidation and deprotection in which the substrate 10 is completely covered with a continuous volume of reagent).

Following receipt by a user of an array 12, it will typically be exposed to a sample (for example, a fluorescently labeled polynucleotide or protein containing sample) and the array then interpreted to obtain the resulting array signal data. Interpretation requires first reading of the array, which may be initiated by scanning the array, or using some other optical or electrical technique to produce a digitized image of the array which may then be directly inputted to a feature extraction system for direct processing and/or saved in a computer storage device for subsequent processing, as will be described herein.

In order to automatically perform feature extraction, the system requires three components for each extraction performed. One component is the image (scan, or the like, as referred to above) itself, which may be a file saved in an electronic storage device (such as a hard drive, disk or other computer readable medium readable by a computer processor, for example), or may be received directly from an image production apparatus which may include a scanner, CCD, or the like. Typically, the image file is in TIFF format, as this is fairly standard in the industry, although the present invention is not limited to use only with TIFF format images. The second component is a grid template or design file (or, alternatively, a grid file, if the user associates such a file for automatic linking with a particular substrate/image via the substrate's identifier 40) that maps out the locations of the features on the array from which the image was scanned and indicates which genes or other entities that each feature codes for.

Figure 3:
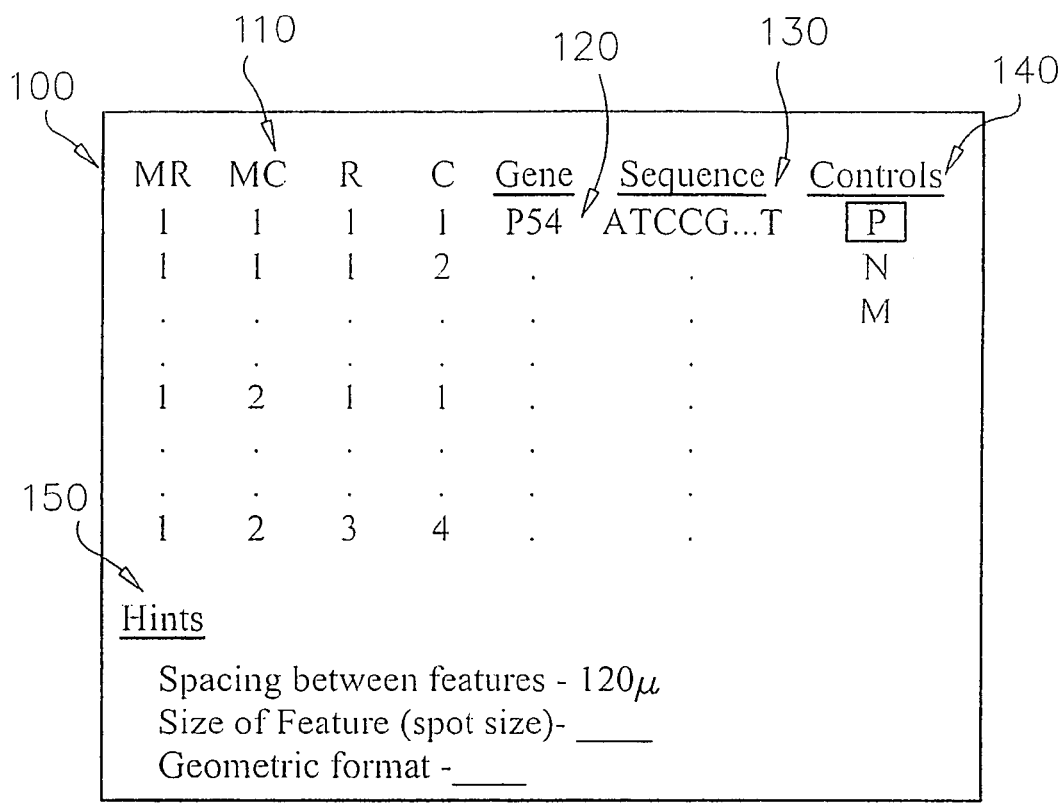
FIG. 3 is a representation of information that may be included in a design file for a grid template.
Figure 4:
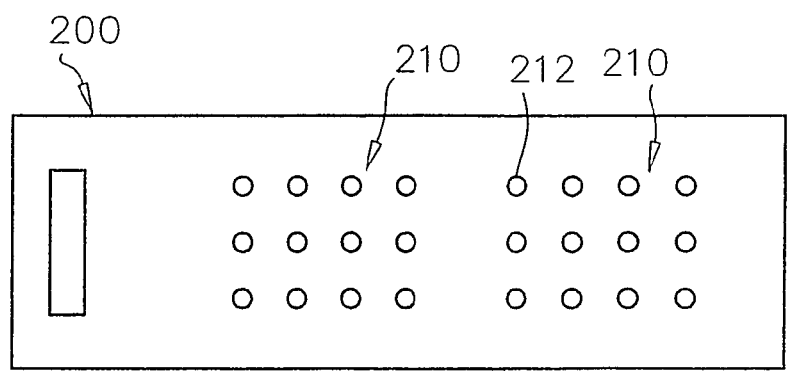
FIG. 4 is a simple illustration of a scanned image, in which the image has two arrays or subarrays each having three rows and four columns of features.

FIG. 3 is a representation of information that may be included in a design file 100 for a grid template. In this example, the feature coordinates 110 are listed for a slide 200 or scanned image thereof having two arrays 210 each having three rows and four columns, see FIG. 4. For each feature on the image, feature coordinates 110 may be provided in design file 100 for the grid template. Each feature may be identified by the row and column in which it appears, as well as meta-row and meta-column, that identify which array or subarray that the feature appears in when there are multiple arrays/subarrays on a single slide 200. Thus, for example, the coordinates that read 1 2 1 1 in FIG. 3 refer to feature 212 shown in FIG. 4, that is in row 1, column 1 of the array located in meta-row 1, meta-column 2. Note that there is only one row of arrays (i.e., one meta-row) and two columns of arrays (i.e., two meta-columns).

For each feature, the gene or other entity 120 that feature codes for may be identified adjacent the feature coordinates. The specific sequence 130 (e.g., oligonucleotide sequence or other sequence) that was laid down on that particular feature may also be identified relative to the mapping information/feature coordinates. Controls 140 used for the particular image may also be identified. In the example shown in FIG. 3, positive controls are used. Typical control indications include, but are not limited to, positive, negative and mismatched. Positive controls result in bright signals by design, while negative controls result in dim signals by design. Mismatched or deletion control provides a control for every probe on the array.

"Hints" 150 may be provided to further characterize an image to be associated with a grid template. Hints may include: interfeature spacing (e.g., center-to-center distance between adjacent features), such as indicated by the value 120μ in FIG. 3; the size of the features appearing on the image (e.g., spot size); the geometric format of the array or arrays (e.g., rectangular, dense pack, etc.), spacing between arrays/subarrays, etc. The geometric format may be indicated as a hint in the same style that the individual features are mapped in 110. Thus, for example, a hint as to the geometric format of slide 200 may indicate rectangular, 1 2 3 4. Hints assist the system in correctly placing the grid template on the grid formed by the feature placement on a slide/image.

The third component required for automatic feature extraction processing is a protocol. The image processing protocol defines the processes that the system will perform on the image file that it is associated with. The system may include a database in which grid templates and protocols may be stored for later call up and association with image files to be processed. The system allows a user to create and manage a list of protocols, as well as a list of grid templates. Both image processing and post processing protocols are user definable and may be saved to allow users flexibility in pre-assigning protocols to specific images or types of images and post processing of outputs from image processing of the specific images or types of images.

The system is adapted to divide or split the analysis of images into two parts: image or pre-processing analysis, and post-processing analysis. This bifurcated processing methodology may help save analysis time in various ways. For example, the user may set up the system to perform the image processing of one or more arrays and view the image processing results one by one.

Image processing may include any or all of: finding the spot (feature) locations of individual features (spots); calculating statistics (e.g., mean intensity signal, median intensity signal; standard deviation of intensity signals, etc.) for individual features; rejection of pixel outliers for individual features, based on statistical calculations; and correlations between pixel intensities read on different channels (e.g., correlation between "red" pixels and "green" pixels for a feature as read on red and green channels of a multi-channel scanner. The input for image processing is an image file produced by scanning a slide (containing an array or plurality of arrays), and is typically provided as a TIFF file, although other formats may be used interchangeably. The output from image processing is typically one or two files, one describing the grid layout of the array/arrays and one describing feature positions, feature centroids and sizes, and optionally other statistics calculated, as indicated above. For example, the output files may be in ".csv" (Comma Separated Values) format (e.g., "feat.csv" and "grid.csv").

Figure 5A:
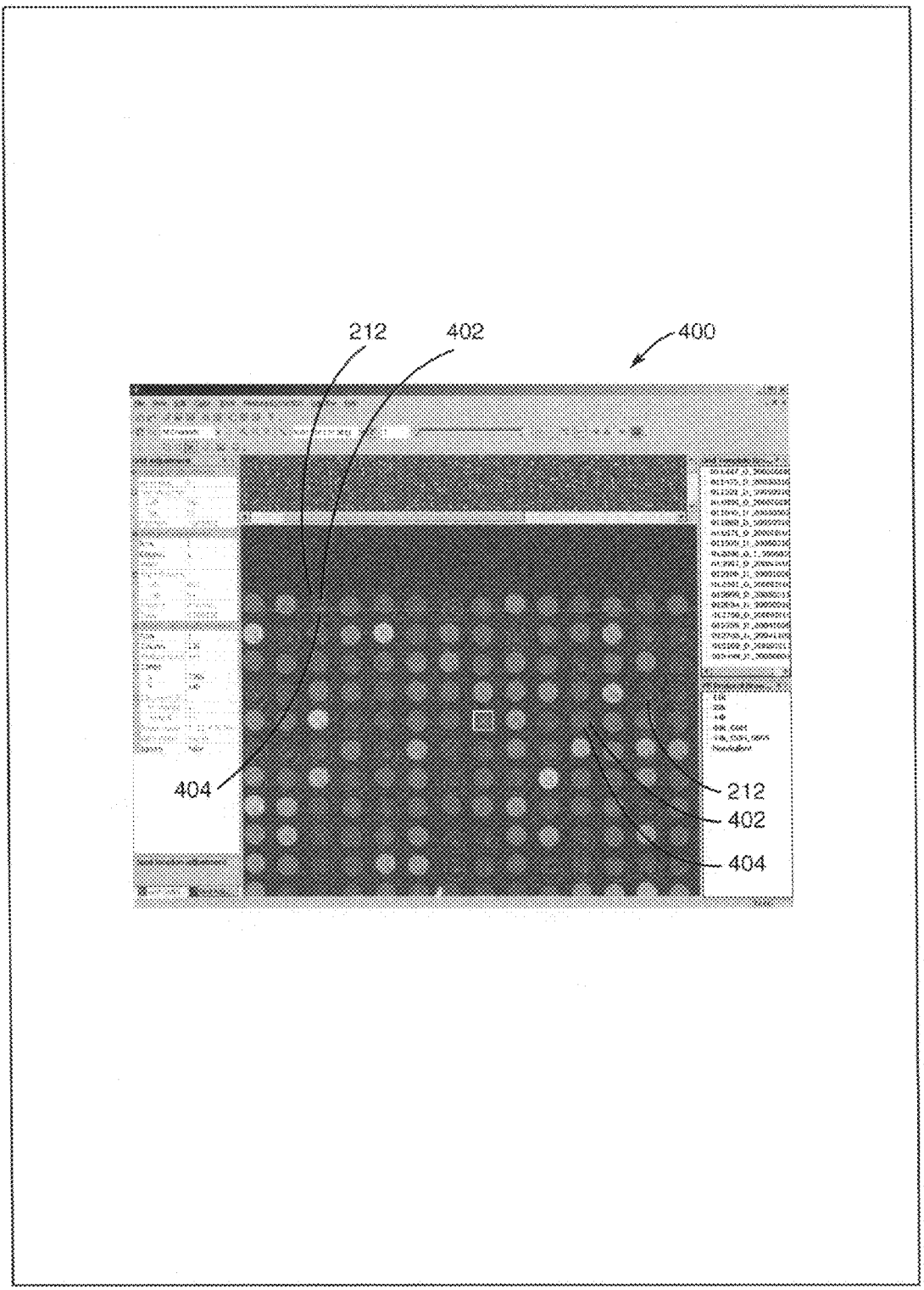
FIG. 5A is a screen shot on a user interface of the system showing an example where the information for locating the features of an array as contained in the grid and feature files outputted from image processing the array, have been loaded into the system and overlaid on top of the image of the array, and where the outputs are unacceptable.

If any image processing result is not satisfactory because either the grid is not laid correctly or the spots are off the grid or some other problem presents that would effect processing results, then the user can manually modify the grid or change the image processing protocol (e.g., dev limit, which is the deviation limit, i.e., the distance from which a spot centroid can deviate from the grid position; or cookie size, which determines the fraction of the feature size (starting from the centroid and working out circumferentially) that is used to calculate feature signal statistics or some other specification) and re-image process it. A determination as to whether or not an image processing result is satisfactory may be made by visual inspection in a preview mode provided by the system, after loading the grid and feature files outputted by the image processing and overlaying these on top of the image that was used as the input for the image processing. FIG. 5A is a screen shot on user interface 400 showing an example where the information for locating the features of an array ad contained in the grid and feature files outputted from image processing the array, have been loaded into the system and overlaid on top of the image of the array. A visual inspection reveals that the grid is shifted as can be clearly observed by the misalignment of some spot boundaries 402 with the corresponding features 212 on the array image. Likewise, the centroids 404 of the cookies spots identified by the spot boundaries 402 are misaligned with the centroids of the features 212 in those instances where the spot boundaries 402 are misaligned.

Figure 5B:
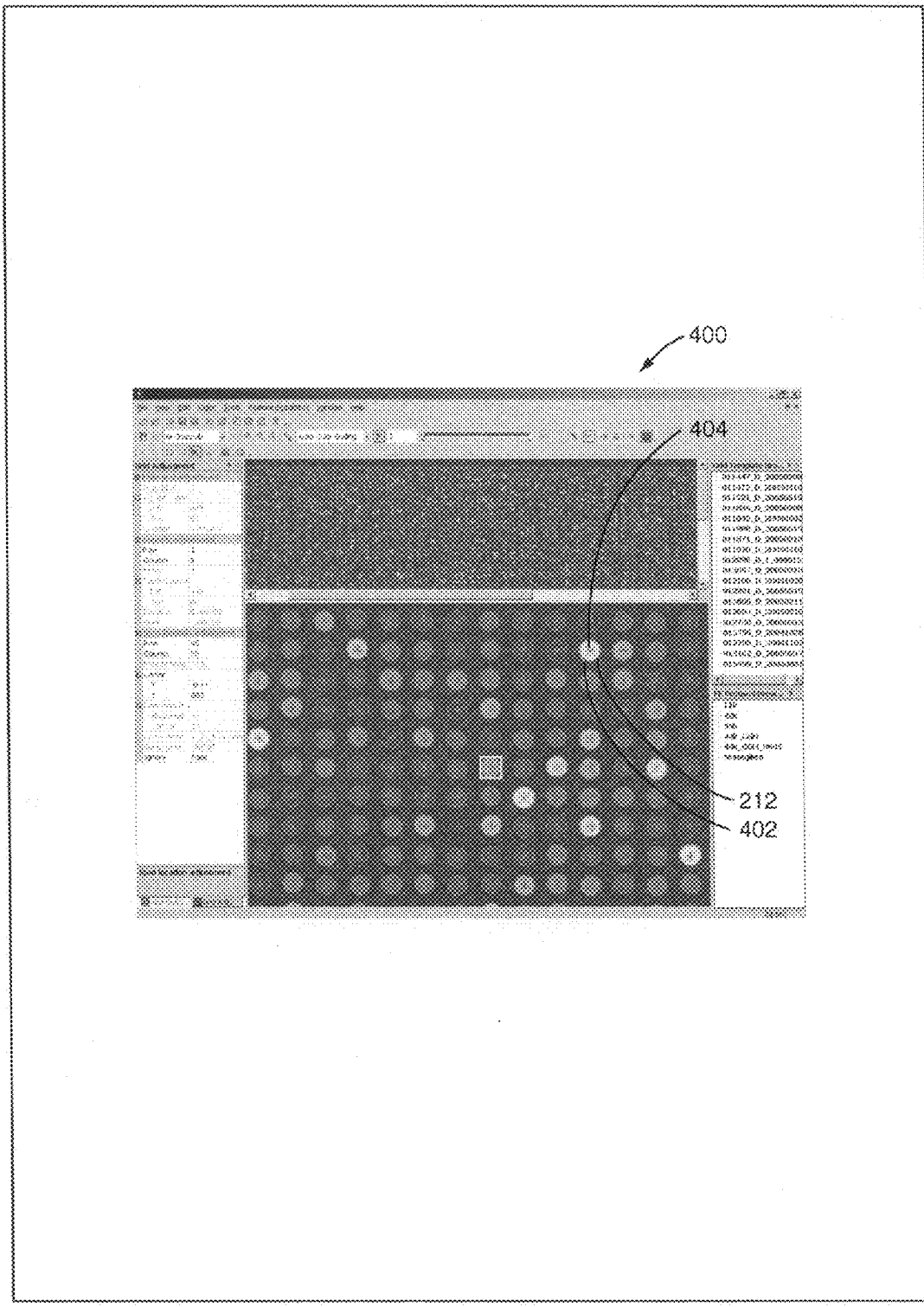
FIG. 5B is a screen shot similar to FIG. 5A, but after modifying the image processing protocol and repeating the image processing of the same array image, using the modified image processing protocol.

If the grid aligns well with the locations of the features on the image, and the spot/feature locations 402 line up with the actual features 212 shown in the image, as in FIG. 5B, for example, then the image processing was satisfactory and the user may decide to move on to post processing. Otherwise, one or more parameters of the image processing protocol may be changed by the user, and then reprocessing of the image processing phase may be carried out in an effort to improve the alignment of the grid and feature files. After this, the preview mode is implemented again for another visual inspection. This process may be iterated as many times as deemed necessary by the user for adequate alignment of the grid and feature locations with the image of the features.

Figure 6A:
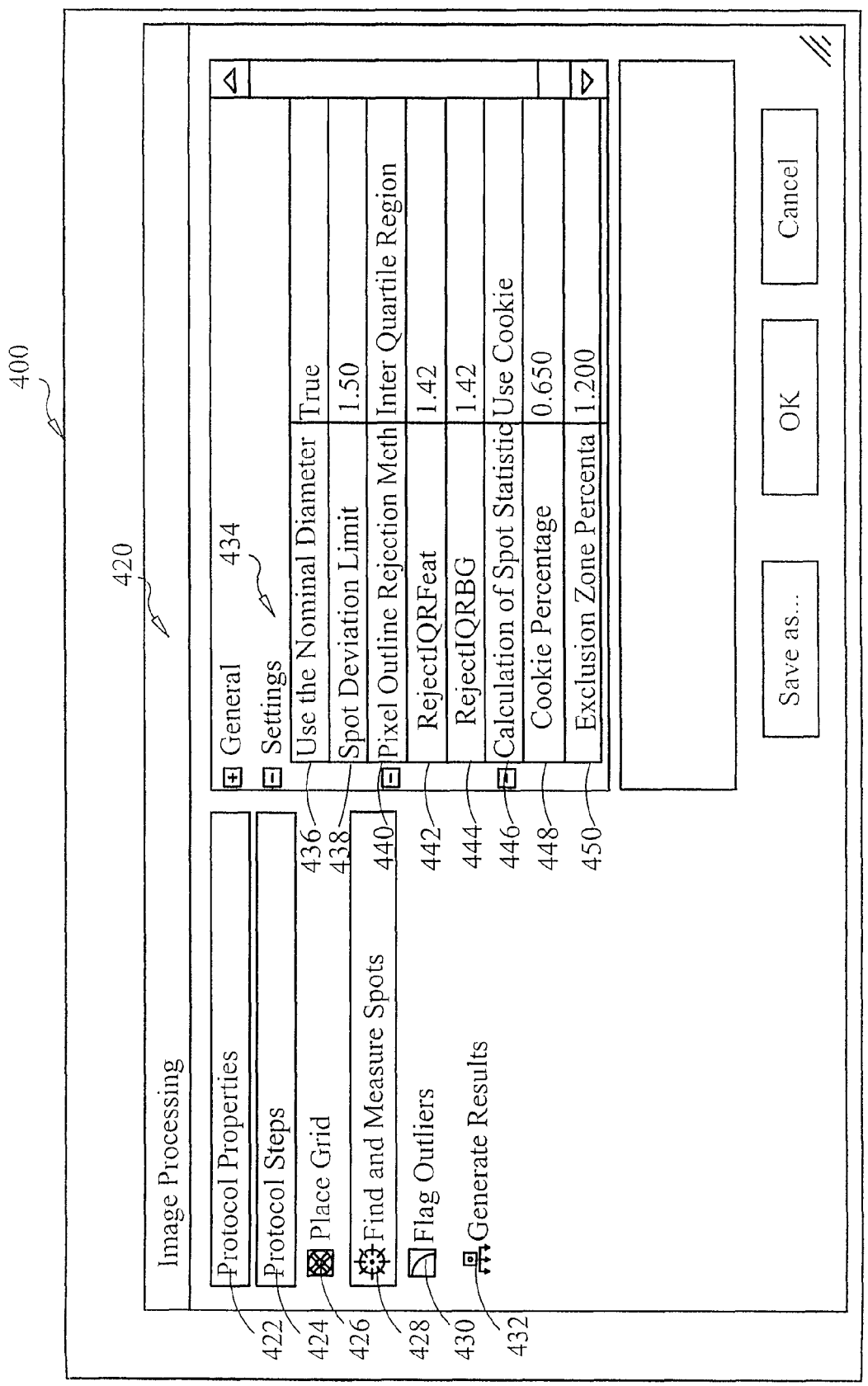
FIG. 6A shows an image protocol editor that may be operated through a user interface of the system in order to select and/or change image processing protocol parameters.

FIG. 6A shows an image protocol editor 420 that may be operated through user interface 400 in order to select and/or change image processing protocol parameters. Note that the image processing protocol may be set to a default image processing protocol, and that the default settings may be displayed upon initially opening the image processing protocol editor 420. The image processing protocol includes protocol properties 422, which, when selected allows a user to select or de-select a protocol step to be carried out during the processing; protocol steps 424, which, when selected, lists the protocol steps currently selected for the processing (note that the protocol steps feature 424 has been selected in FIG. 5A and that the protocol steps are displayed, where steps shown include Place Grid 426, Find and Measure Spots 428, Flag Outliers 430 and Generate Results 432). A feature for generating results 432 may be selected by the user once the array image has been loaded and the user is satisfied with the image processing protocol settings and grid template to be applied are as desired, at which time image processing automatically proceeds, using the selected image processing protocol and grid template.

FIG. 6A shows the "Find and Measure Spots" feature having been selected by the user in the image processing protocol editor interface 420, after listing the protocol steps. The settings for the "Find and Measure Spots" feature 428 that may be selected and/or edited are listed in the settings window 434 and include "Use the Nominal Diameter" 436, "Spot Deviation Limit" 438, "Pixel Outlier Rejection Method" 440, "RecjectIQRFeat" 442, "RejectiIQRBG" 444, "Calculation of Spot Statistic" 446 "Cookie Percentage" 448" and "Exclusion Zone Percentage" 450. The "Use the Nominal Diameter" setting 436 may be set to True or False. When set to "True", a preset nominal diameter for finding spot size is used as an initial value in calculating spot size. When set to "False", the initial value for calculating spot size is received from the output of a grid finding algorithm used to locate the grid on the array. Details about this grid finding algorithm are described in co-pending, commonly assigned application Ser. No. 10/449,175 filed May 30, 2003 and titled "Feature Extracting Methods and Systems", which is hereby incorporated herein, in its entirety, by reference thereto. The "Spot Deviation Limit" setting 438, is set to a distance value that is the maximum distance from which a spot centroid can deviate from the grid position and still be successfully located. "Pixel Outlier Rejection Method" 440 has been selected as the inter quartile region method in FIG. 6A. where pixel intensities for a spot are ranked according to intensity and the pixel intensities between the $25^{th}$ and $75^{th}$ quartile of this ranking are scaled by the RejectIQRFeat setting of 1.42. This range is then applied to the unscaled ranking of pixel intensities, and those pixel intensities that fall outside of the scaled range are rejected as outliers. Only those pixel intensity values not rejected as outliers are then used as the pixels to determine the other statistics for the spot, such as spot size, spot signal intensity, etc. Other pixel outlier rejection methods that may be selected may include standard deviation based statistical methods of selecting outliers, and other known statistical methods for determining outliers. "RecjectIQRFeat" 442 is a user-settable scaling factor by which the range is scaled for use in selecting outliers, as described above. Similarly, "RejectiQRBG" 444 is a user-settable scaling factor by which a range of background intensity pixels may be scaled for use in selecting background pixel outliers. "Calculation of Spot Statistic" 446 in FIG. 6A has been selected to "Use Cookie", meaning that the cookie size is used as a basis for calculating feature intensity statistics. Other settings that may be selected for the calculation of the spot statistic include calculating feature intensity statistics based on the entire spot or feature size that is determined by the image processing. "Cookie Percentage" 448' has been set to 0.65 in FIG. 6A, which means that the central most 65% of the feature outlined by the cookie is used in calculating the feature signal statistics. "Exclusion Zone Percentage" 450 has been set to 1.200, which means that for a spot radius of 1.0, the area circumscribing the centroid of that spot, from a radius of 1.0 to a radius of 1.200 is excluded from statistical calculations for either feature intensity or background intensity. This is because this area is considered a transition zone, where some pixel intensities may represent the feature and some may represent background, and as such, this area introduces excessive noise. The Exclusion Zone Percentage may be modified by a user.

Figure 6B:
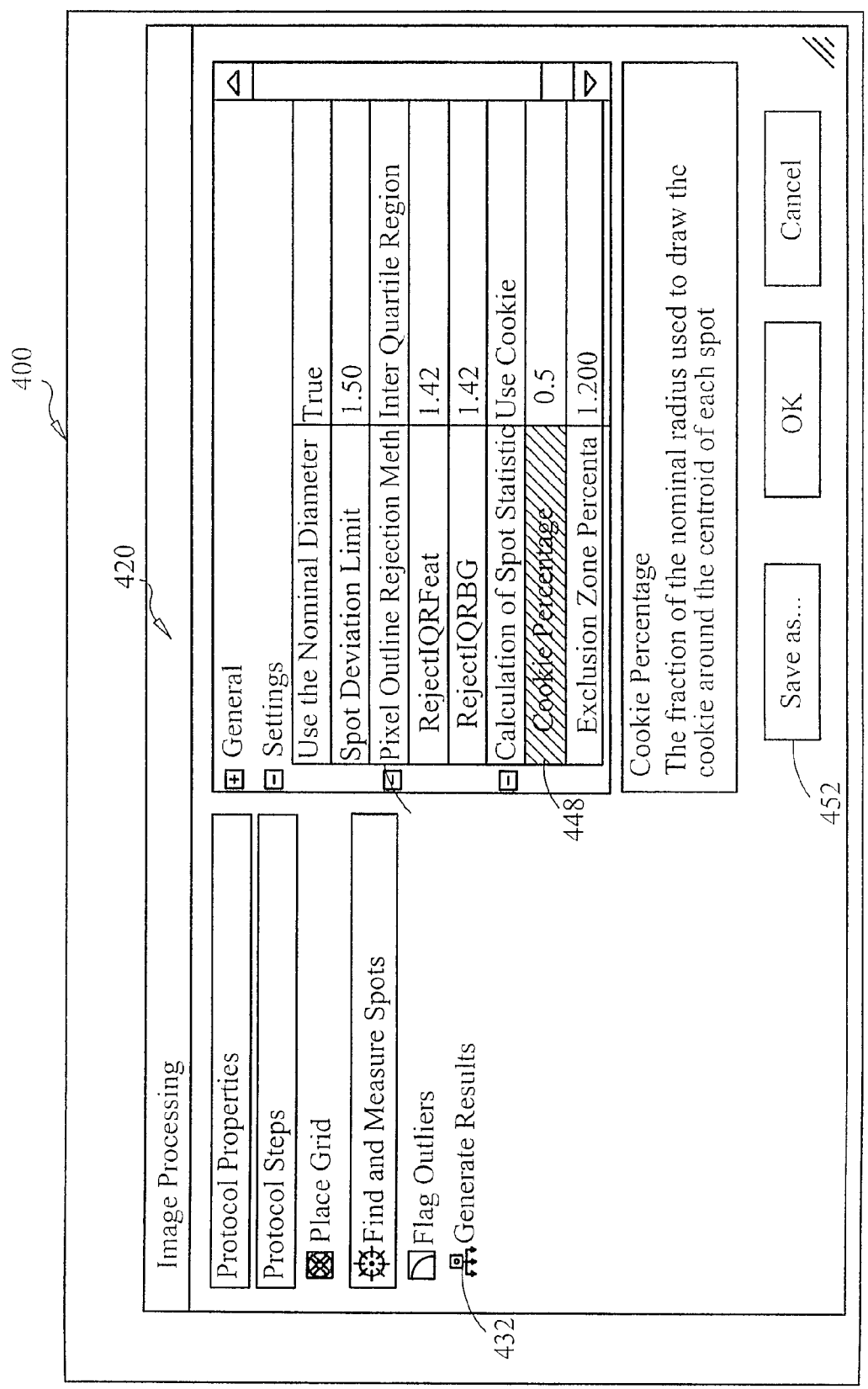
FIG. 6B shows the image protocol editor of FIG. 6A, after a parameter has been modified.

As noted above, if upon preview of the image processing outputs overlaid on the image of the array that was processed, it is determined by a user that the outputs from that image processing were unsatisfactory (e.g., see FIG. 5A), then the user may elect to re-image process that same array image, after modifying the image processing protocol. FIG. 6B shows an example where a user has modified the image processing protocol via image process protocol editor 420 of user interface 400. In this example, assume that image processing of an array was performed using a first image processing protocol, the "Find and Measure Spots" settings 428 of which are shown in FIG. 6A. After previewing the output of the image processing, overlaid on the array image (likes shown and described with regard to FIG. 5A), the user determined, upon visual inspection, that the outputs did not adequately align with the actual features 212 on the array image. In this case, the user may go back into the image processing protocol editor 420 and change the image processing protocol, then image process the array image again.

In the example shown in FIG. 6B, the user has maintained all settings as were in the image processing protocol for the image process already completed, except for the cookie percentage setting, which has been changed from 0.65 to 0.5. After adjusting the protocol as desired, the user may then want to save this modified protocol to a local data base of image processing protocols, and can do this by selecting the "Save As" button 452 and identifying a file name by which the modified protocol will be saved, and a location where the file will be saved. With or without saving, the user may initiate an image processing of the array image by selecting the "Generate Results" feature 432 of the interface 420, whereby the array image is then automatically image processed using the new image protocol settings. A preview of the new results can then be carried out to confirm whether or not the new image processing outputs are satisfactory. If they are not, then this process can be iterated as many times as the user finds necessary to produce adequate image processing outputs.

Once the result (image processing output) is satisfactory, the user can save the output of the image-processing step in the form of the grid and feature files described above. This approach may be very useful for certain substrates produced by less well-known manufacturers, which may employ array patterns not typically used by the larger manufacturers and/or may not have the same quality control standards as the more well-known manufacturers. The outputs from the image processing steps can then be used to complete the post processing analysis in an automated batch, where an automated batch process is one in which data from all of the image processing output files, used as input to the automated batch, are processed together, in a single automated process. Thus, outputs from at least two image processes are loaded into a batch project, and these inputs are automatically post processed.

The inputs may be sequentially post-processed (although all in a continuous, automated process, with no human intervention required) in some aspects of the invention, or, in other aspects, partially or totally combined and processed at the same time. At least one of the inputs (image processing outputs) may be feature post-processed based upon a different grid template or protocol than at least one other of the inputs. Further details regarding automated batch processing may be found in co-pending, commonly owned application Ser. No. 10/941,501 filed Sep. 15, 2004 and titled Automated Feature Extraction Processes and Systems", which is hereby incorporated herein, in its entirety, by reference thereto. As noted above, post-processing may include processing for background subtraction (of any type, including, but not limited to local background subtraction, negative-control based background subtraction, spatial de-trending, etc.), dye normalization, error models, and calculation of signal intensity ratios between signals read on two channels (with or without background subtraction, dye normalization and/or any of the other post-processing calculations). An output from the most current image processing step may be inputted directly for post-processing, along with inputted stored output files from the arrays that were image processed previously, the results of which were stored.

Figure 7:
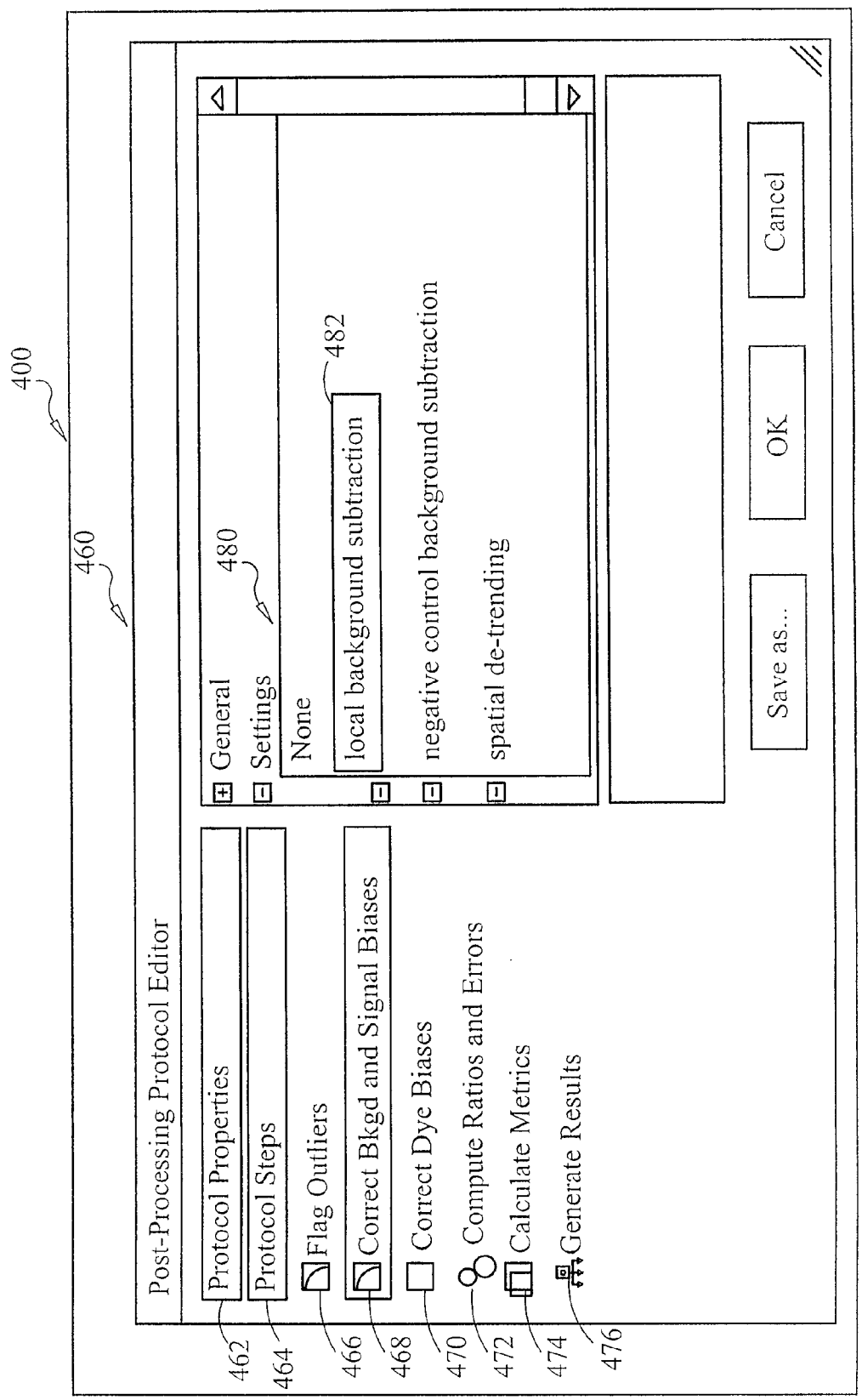
FIG. 7 shows a post-processing protocol editor that may be operated through a user interface of the system in order to select and/or change post-processing protocol parameters.

FIG. 7 shows a post-processing protocol editor 460 that may be operated through user interface 400 in order to select and/or change post-processing protocol parameters. Note that the post processing protocol may be set to a default post processing protocol, and that the default settings may be displayed upon initially opening the post processing protocol editor 460. The post-processing protocol editor interface 460 includes protocol properties 462 which, when selected allows a user to select or de-select a protocol step to be carried out during the processing; protocol steps 464, which, when selected, lists the protocol steps currently selected for the processing (note that the protocol steps feature 464 has been selected in FIG. 7 and that the protocol steps are displayed, (note that the steps displayed include Flag Outliers 466, Correct Bkgd and Signal Biases 468, Correct Dye Biases 470, Compute Ratios and Errors 472, Calculate Metrics 474 and Generate Results 476). For each of the features flag outliers 466, Correct background and signal biases 468, Correct dye biases 470, Compute ratios and errors 472 and Calculate metrics 474, these features may be deselected by selecting protocol properties 462 and interactively de-selecting, via interface 400, the steps that a user does not want the automated process to carry out.

In the view shown, the Correct Background and Signal Biases feature 468 has been selected. Accordingly, the choices and setting for this feature are displayed in the settings window 480. As shown, the user has selected local background subtraction 482.

Figure 8:
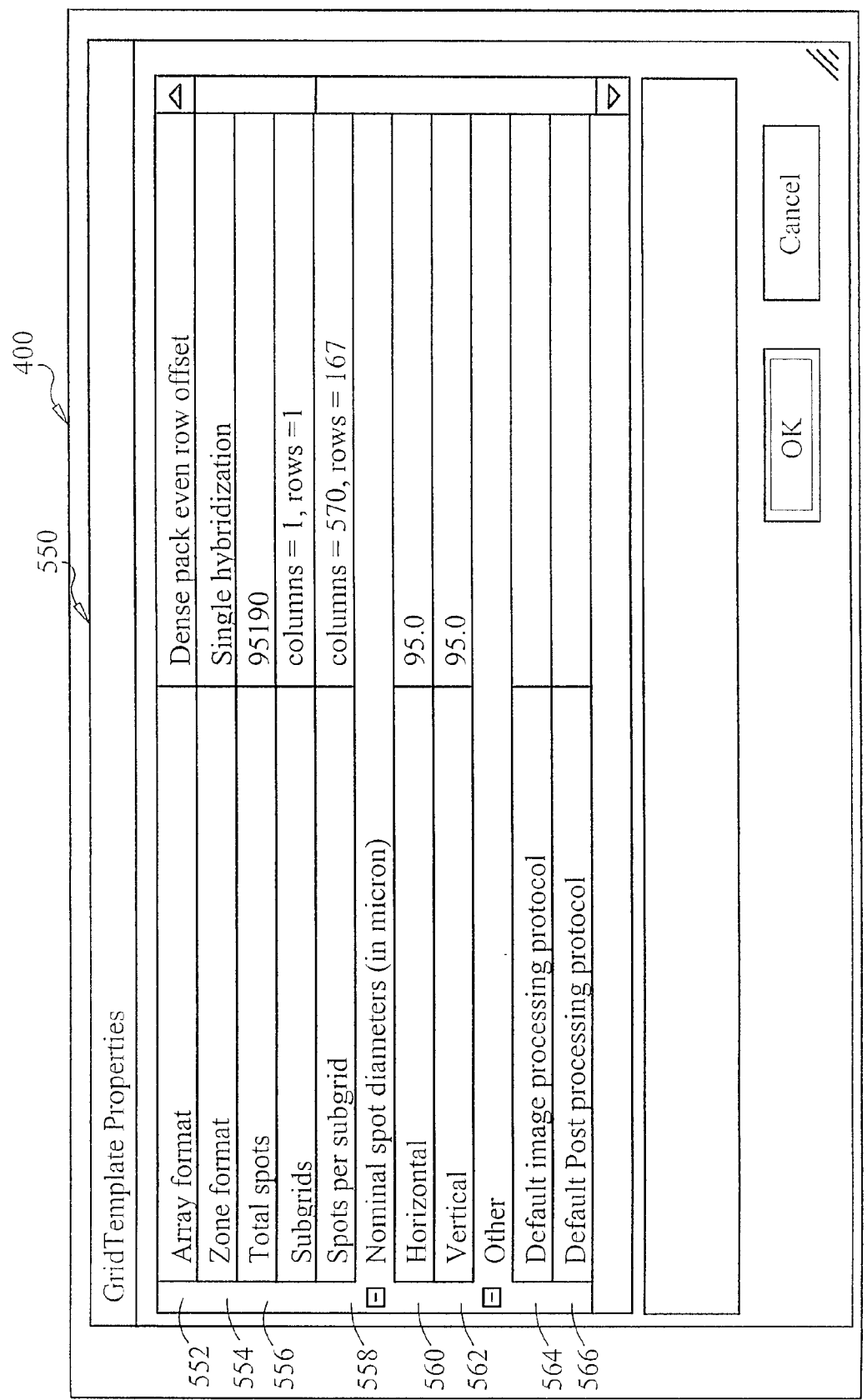
FIG. 8 shows an example of a grid template 550 displayed on a user interface of the system.

For each grid template, a user may assign an image processing protocol and a post-processing protocol, for image processing and post processing, respectively. As noted, default image processing and post processing protocols may be assigned in instances where a user wants to keep the default assignments. FIG. 8 shows an example of a grid template 550 displayed on user interface 400. The grid template shown includes parameters identifying the array format 552, zone format 554, total number of spots (features) 556 on the substrate, which may include an array, or a plurality of arrays (sub-arrays), number of subgrids 558 (in this case, only one array is present as indicated by columns=1 and rows=1), number of spots per subgrid 558 (identified by number of columns and rows), and nominal spot diameters in both the horizontal 560 and vertical 562 directions. Additionally, the grid template may identify the image processing and post processing protocols that have been assigned to run with it during image processing and post processing, respectively. In this example, the default protocols are assigned for both image processing and post processing. The assignments of the image processing and post processing protocols may be modified by a user.

Figure 9:
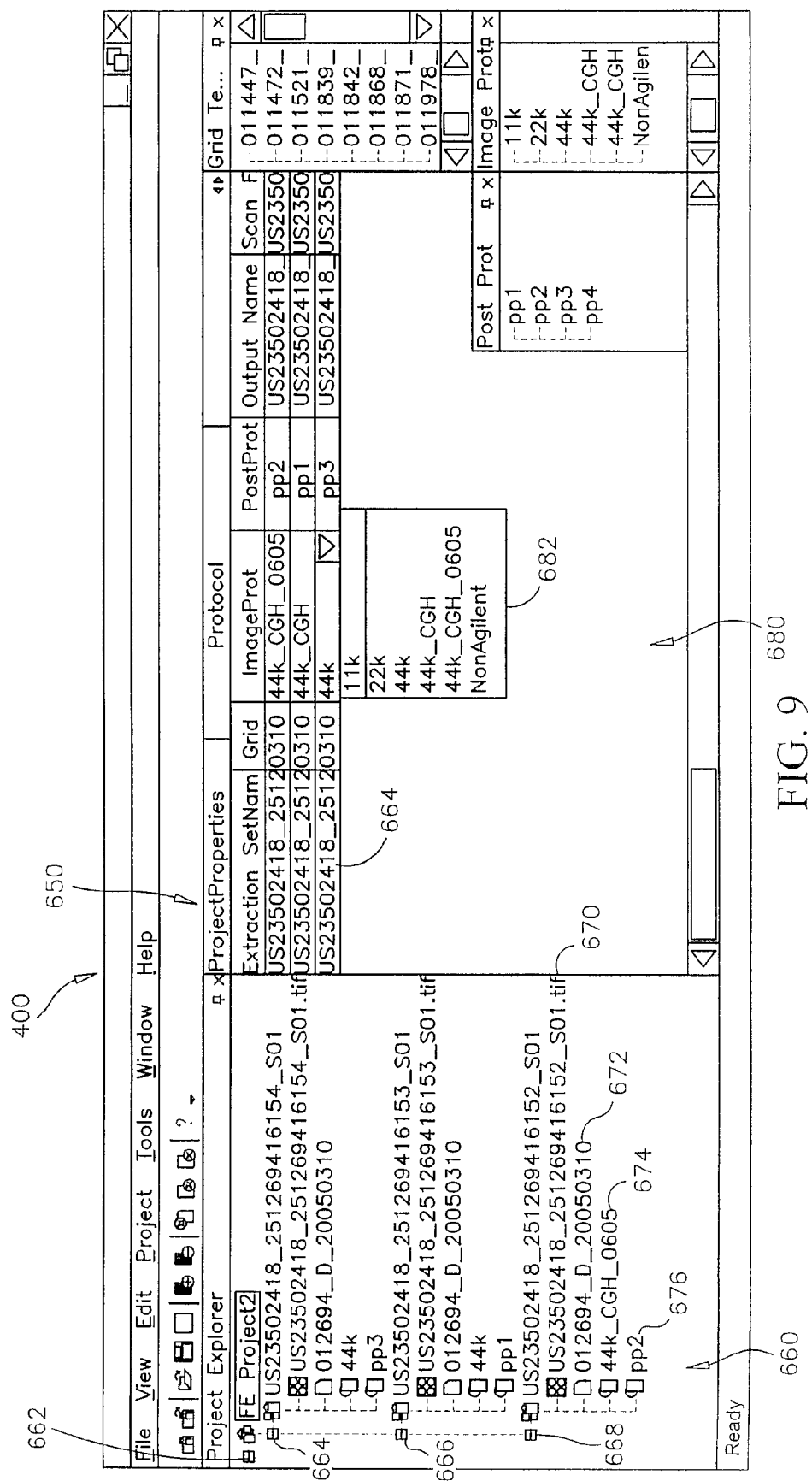
FIG. 9 shows a display of a project manager interface that allows a user to assign image protocols and post processing protocols to each image.

FIG. 9 shows a display of a project manager interface 650 on user interface 400 that allows a user to assign image protocols and post processing protocols to each array image. A project tree 660 may be created for automated batch processing, for image processing and/or for post processing. In the example shown, FE Project 2 662 includes three arrays 664, 666, 668. The tree also lists the image file 670, grid template 672, imager processing protocol 674 and post processing protocol 676 that apply to each array. In the editor window 680, a user may select and modify assignments of image processing and post processing protocols to any array to be processed according to its associated grid template. In the example shown, the image protocol assignment for array 664 has been selected for assigning an image protocol, whereupon a drop down menu 682 appears with protocol selections from which to choose. Assignments of post processing protocols may be made in the same manner. Further details regarding project management may be found in co-pending, commonly owned application Ser. No. 10/941,501.

Thus, when using the current system, when working with a multi-pack image (a substrate having a plurality of arrays or sub-arrays thereon), for example, the system may input and/or save the image file as a single image for image processing treatment, i.e., no splitting of images (e.g., into an image file for each array/sub-array) is required. Accordingly, pre-processing (image processing) of all of the arrays/sub-arrays may be performed together, on the image of the substrate as a whole. Post-processing may then be carried out on individual arrays or sub-arrays, as characterized by the image processing, and output files for the post-processing of each array/subarray may be provided and stored.

As another example of advantages provided by the present system and methodologies, an advanced user may want to try out different post processing protocols (e.g. different background subtraction methods or a different dye-normalization method) in order to get the most accurate result from his/her experiment. If the outputs from the image processing steps are acceptable and there is no need to change anything then the user may run a batch with the same image and same image processing protocol but with different post processing protocols associated with different instances of the same image to be processed. In order save time the user may even save the output from image-processing step once and associate it with the same image (e.g., TIFF image) and different post processing protocols in the batch.

Separation of pre-processing and post-processing steps during feature extraction processing of array images provides additional flexibility in the manner that data can be analyzed. For example, the present invention allows interarray analysis. A user may want to do the analysis (post processing) of data from multiple arrays in a combined fashion. The present system may image process substrates or images of substrates, or even arrays from the same substrate separately as the grids and spot/feature sizes of each substrate, image or array may vary from one to another. After separate image processing of the arrays to be analyzed, the system may then combine the outputs of the image processing steps of the multiple arrays (e.g. mean signal and/or other statistics as described above, from each spot) and do a combined post processing analysis of image processed data all at once.

As another example, arrays may be pre-processed together, and then the results of pre-processing may be split to post-process the different arrays separately. Division spaces between arrays on a single substrate are typically located by their identification in the grid template employed for the image processing (pre-processing), as may be determined from the parameters such as described above with regard to FIG. 8, for example. If grid template parameters are not available, the projection based grid finding algorithm described in application Ser. No. 10/449,175 groups features/spots according to regular spacings between features and identifies division spaces by their significantly greater distance, compared to interfeature spacing.

One example where a user may want to employ the approach of image processing multiple array images together and then post processing individual arrays, is when multiple arrays are provided on a "multipack" substrate, where the arrays are all formed according to the same layout, specifications and each may even have the same probes, but where the arrays have been hybridized differently. In this case, there is a definite advantage of doing image processing of the whole slide (inter-array image processing) compared to image-processing of individual arrays on the slide, which is described in more detail in the following paragraphs. However, the post processing parameters of those individual packs may be different, such as when they have been hybridized differently, for example. Since the architecture of the system is split into features enabling separate imaging and post processing, the present system has the capability to analyze multi-pack arrays in the manner described.

In still another example, several arrays may be image processed separately, and the results of these image processes may be combined to post process them together in a single process (automated batch process), such as where a user may use a protocol with a goal to normalize results between arrays (inter-array normalization). Thus, arrays having the same features may be processed according to different image processing protocols, and the results of these processes are then combined to post process all results together.

As another example, multiple replicate arrays may be image processed separately or sequentially, and the results (outputs) of these image processes may be combined, feature by feature, where outputs of all replicates of a feature are combined, per feature, for post processing on a combined virtual array after combining the replicates.

As noted, the system is adapted to image process an entire slide/image, but post process per hybridization. Thus, a multipack image may be initially processed to grid all of the arrays together for location of features. Once features have been located, divisions between the arrays are determined, and each array is processed individually as to post processing (e.g., background subtraction, dye normalization, etc.) to determine the results for each array individually.

Figure 10:
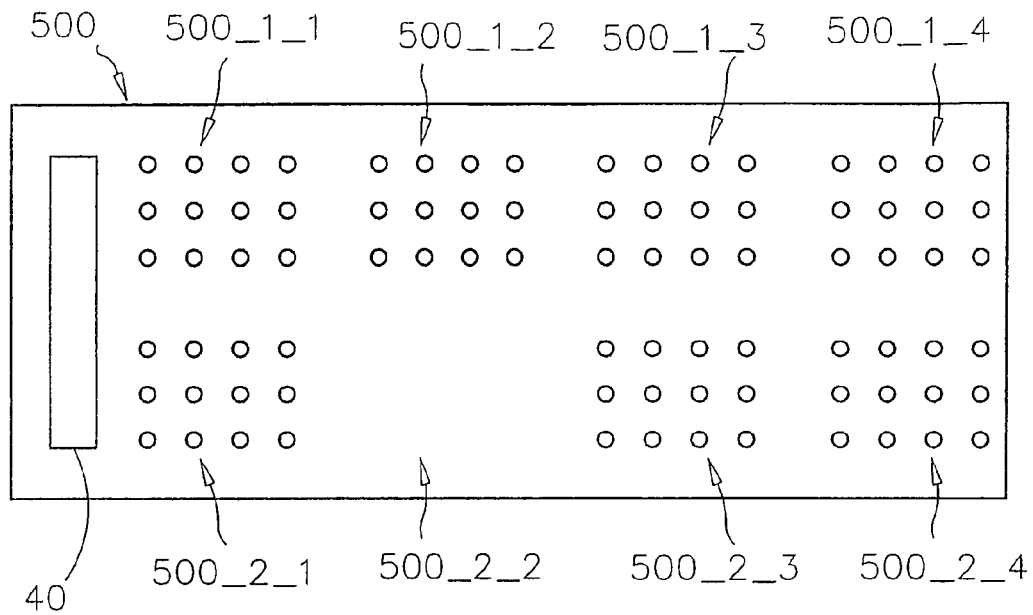
FIG. 10 is a simple illustration representing an eight pack scanned image, including one array that was a "mock hyb".

There are distinct advantages to image processing the entire image containing multiple arrays. One advantage is that, for substrates containing a plurality of arrays or sub-arrays, when the geometries of the arrays deposited on the same substrate are similar, there is redundancy provided by the repeating pattern of the array when all are considered together. This may be particularly useful when some features in various arrays are dim or non-existent and it would thus be difficult to locate the grid accurately based on intensities of features of that particular dim array. By relying upon the brighter features of adjacent array/sub-arrays, the system is able to locate the grid more accurately for the array/subarray containing the dim features. Even more prominent is the advantage gained in identifying features in an array where no features are readily detectable, by relying on the gridding locations provided by gridding the arrays together. An example of this is schematically shown in FIG. 10 wherein array image 500_2_2 of multipack image 500 represents a "mock hyb" (i.e., array the probes of which have not been hybridized). In such a situation, it is algorithmically more advantageous to find the grid positions of all the individual arrays together rather than one array at a time. The repeated pattern of the grid for each array/sub-array helps to detect the grid of the array having very dim intensity, which is otherwise undetectable without the data relied upon from the other arrays/sub-arrays on the substrate. Further information regarding algorithmic considerations for locating features can be found in application Ser. No. 10/869,343 filed Jun. 16, 2004 and titled "System and Method of Automated Processing of Multiple Microarray Images" and in application Ser. No. 10,449,175. Application Ser. Nos. 10/869,343 and 10,449,175 are hereby incorporated by reference herein, in their entireties, by reference thereto. In the disclosure of application Ser. No. 10/869,343, it is not possible to split the image processing and post processing steps of the analysis, and images are cropped to provide eight single array images from and eight pack multi array image. The present system is capable of imaging the eight pack as a single image, as already noted, therefore the user need only save one image file, as opposed to eight.

After the grid is laid and the system has calculated signal statistics (e.g., mean spot signals for the colors, standard deviations for the spot signals for each color, etc.) for each feature, the system moves to post processing. Post processing in this instance is done on a per array basis, rather than a per image basis, since each array typically has a different hybridization and may need a different protocol for data analysis. Also, since the hybridizations are separate the user will typically want separate outputs corresponding to the separate arrays. Post processing may include background subtraction processing, outlier rejection processing, dye normalization, and finding/calculating expression ratios. The protocols for image or post processing are typically XML files that contain the parameters of the algorithms to be used in feature extracting an array image.

Figure 11:
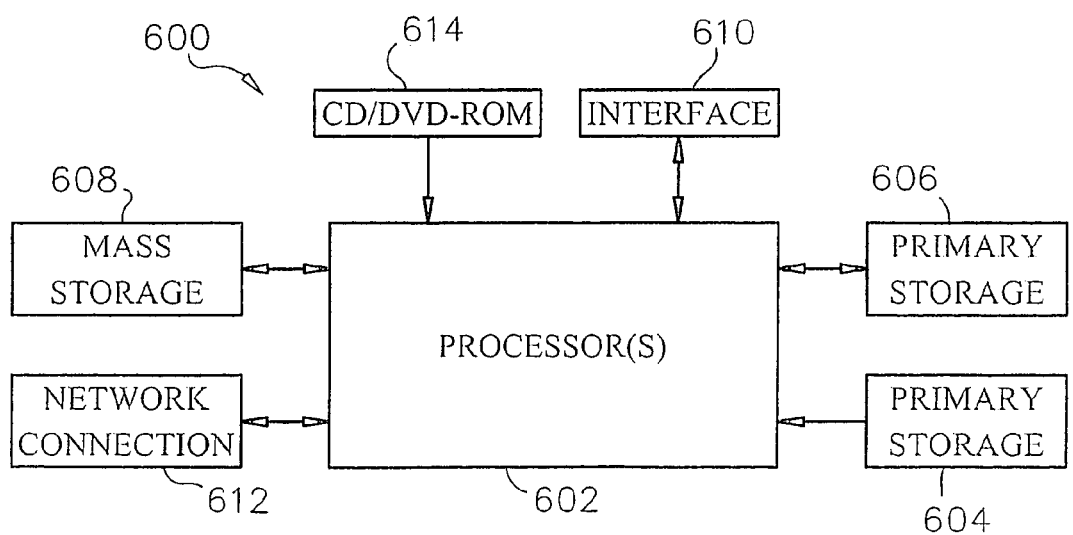
FIG. 11 illustrates a typical computer system that may be used to practice an embodiment of the present invention.

FIG. 11 illustrates a typical computer system that may be used to practice an embodiment of the present invention. The computer system 600 includes any number of processors 602 (also referred to as central processing units, or CPUs) that are coupled to storage devices including primary storage 606 (typically a random access memory, or RAM), primary storage 604 (typically a read only memory, or ROM). As is well known in the art, primary storage 604 acts to transfer data and instructions uni-directionally to the CPU and primary storage 606 is used typically to transfer data and instructions in a bi-directional manner Both of these primary storage devices may include any suitable computer-readable media such as those described above. A mass storage device 608 is also coupled bi-directionally to CPU 602 and provides additional data storage capacity and may include any of the computer-readable media described above. Mass storage device 608 may be used to store programs, data and the like and is typically a secondary storage medium such as a hard disk that is slower than primary storage. It will be appreciated that the information retained within the mass storage device 608, may, in appropriate cases, be incorporated in standard fashion as part of primary storage 606 as virtual memory. A specific mass storage device such as a CD-ROM or DVD-ROM 614 may also pass data uni-directionally to the CPU.

CPU 602 is also coupled to an interface 610 that includes one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 602 optionally may be coupled to a computer or telecommunications network using a network connection as shown generally at 612. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions for population of stencils may be stored on mass storage device 608 or 614 and executed on CPU 608 in conjunction with primary memory 606.

In addition, embodiments of the present invention further relate to computer readable media or computer program products that include program instructions and/or data (including data structures) for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; optical media such as CD-ROM, CDRW, DVD-ROM, or DVD-RW disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of operating a data processing system comprising at least one hardware computing element to extract features from an image obtained from a plurality of chemical arrays, said method comprising:
    bifurcating processing of said image using said at least one hardware computing element of said data processing system by performing image processing and post-processing,
    said image processing comprising processing parts of said image, each part corresponding to a different one of said plurality of arrays in an automated batch process, to produce image-processed outputs that are different from said image and contain information extracted from said image;
    and said post-processing comprising processing said image-processed outputs according to different post-processing protocols with respect to different ones of said parts of said image corresponding to at least two of the plurality of the arrays, to produce post-processed outputs; and outputting at least one of said image-processed outputs and/or at least one of said post-processed outputs.

2. The method of claim 1, further comprising assigning the different post-processing protocols to at least two of said image-processed outputs, each post-processing protocol corresponding to a different one of said plurality of arrays, wherein said post-processing is carried out automatically, after said image processing, according to the post processing protocols assigned to said image-processed outputs.

3. The method of claim 1, wherein the plurality of the arrays are located on a single substrate, and said image processing in a batch mode includes gridding all of the arrays together in a single gridding step.

4. A method of operating a data processing system comprising at least one hardware computing element to extract features from an image obtained from a plurality of chemical arrays, said method comprising:

bifurcating processing of said image using said at least one hardware computing element of said microarray feature processing system by performing image processing and post-processing, said image processing comprising processing a part of said image corresponding to only one of said plurality of arrays to produce image-processed outputs that are different from said image and contain information extracted from said image; and said post-processing comprising processing one of said image-processed outputs in an automated batch process, including assigning to said output at least two different post-processing protocols, and outputting a post-processed output for each said processing protocol; and outputting at least one of said image-processed outputs and/or at least one of said post-processed outputs.

5. The method of claim 4, wherein said image processing an array comprises image processing a plurality of said parts of said image in an automated batch process, using image processing parameters that are the same for each part to produce image-processed outputs corresponding to said plurality of arrays, and wherein said assigning at least two different post-processing protocols comprises assigning a first of said at least two different post-processing protocols to at least a first of said image-processed outputs corresponding to one of said plurality of arrays and assigning a second of said at least two different post-processing protocols to at least a second of said image-processed outputs corresponding to another of said plurality of arrays.

6. The method of claim 5, wherein the plurality of said arrays are located on a single substrate.

7. The method of claim 4, wherein said at least two different post-processing protocols each include at least one difference in at least one of background subtraction algorithms, dye-normalization algorithms and ratio finding algorithms, of said at least two different post-processing protocols.

8. The method of claim 4, further comprising:

storing said output of said image processing;

repeating said image processing and said storing said output of said repeated image processing for at least one iteration;

accessing the stored outputs of said image processings, and inputting outputs of at least two iterations of said image processing for said post-processing said results in an automated batch process.

9. A method of operating a data processing system comprising at least one hardware computing element to perform inter-array analysis on a set of images comprising at least one image, said set obtained from a plurality of chemical arrays, said method comprising:

image processing using said at least one hardware computing element a first part of said set of images corresponding to a first array with a first image processing protocol to obtain a first image-processed output that is different from said set of images and contains information extracted from said set of images;

image processing using said at least one hardware computing element a second part of said set of images corresponding to a second array with a second image processing protocol to obtain a second image-processed output that is different from said set of images and contains information extracted from said set of images;

combining said first and second image processed outputs to obtain combined image-processed outputs;

post-processing said combined image-processed outputs corresponding to said first and second arrays in an automated batch process to obtain post-processed outputs; and outputting at least one of said image-processed outputs and/or at least one of said post-processed outputs.

10. The method of claim 9, further comprising comparing processed outputs resulting from said post processing of said first output from image processing of said first array with processed outputs resulting from said post processing of said second output from image processing of said second array, and outputting comparison results.

11. The method of claim 9, wherein said first image processing protocol differs from said second image processing protocol.

12. The method of claim 9, wherein said first image processing protocol is the same as said second image processing protocol.

13. The method of claim 9, wherein said first array is located on a first substrate and said second array is located on a second substrate.

14. The method of claim 9, wherein said first and second arrays are located on a single substrate.

15. The method of claim 9, wherein said first image-processed output comprises mean intensity signals calculated for features on said first array and said second image-processed output comprises mean intensity signals calculated for features on said second array.

16. A method of operating a data processing system comprising at least one hardware computing element to extract features from an image obtained from multiple arrays contained on a single substrate, said method comprising:

image processing parts of said image using said at least one hardware computing element, each part corresponding to a different one of said multiple arrays, in an automated batch process, to produce image-processed outputs that are different from said image and contain information extracted from said image;

post-processing said image-processed outputs corresponding to individual arrays, according to at least two post-processing protocols to produce post-processed outputs, wherein said post processing includes individually assigning a post-processing protocol to each of said parts of said image corresponding to each of said multiple arrays, and wherein at least two of the post-processing protocols are different from one another; and outputting at least one of said image-processed outputs and/or at least one of said post-processed outputs.

17. The method of claim 16, wherein said image includes gridding all of said parts of said image corresponding to said multiple arrays simultaneously and locating all features of each of said parts of said image corresponding to said multiple arrays.

18. The method of claim 17, wherein said image processing further includes identifying division spaces between said parts of said image corresponding to different ones of said arrays.

19. The method of claim 16, wherein each array of said multiple arrays has the same geometrical layout of features compared to all other arrays of said multiple arrays, and wherein at least two of said arrays have been hybridized differently from each other.

20. An automated feature extraction bifurcation system for processing chemical arrays, said system including firmware-implemented, software-implemented or a combination of firmware-implemented and software-implemented logic that implements the method of claim 4.

21. An automated feature extraction bifurcation system for performing inter-array analysis, said system including firmware-implemented, software-implemented or a combination of firmware-implemented and software-implemented logic that implements the method of claim 9.

22. An automated feature extraction bifurcation system for processing multiple arrays contained on a single substrate, said system including firmware-implemented, software-implemented or a combination of firmware-implemented and software-implemented logic that implements the method of claim 16.

23. A non-transitory computer readable medium storing one or more sequences of instructions which, when said medium is accessed by one or more data processors including at least one hardware computing element, are executed by said one or more data processors, control a data analysis process to extract features from an image obtained from multiple arrays contained on a single substrate, said instructions comprising:

image processing parts of said image using said at least one hardware computing element, each part corresponding to a different one of said multiple arrays in batch mode to produce image-processed outputs that are different from said image and contain information extracted from said image;

post-processing said image-processed outputs according to different post-processing protocols with respect to different ones of said parts of said image corresponding to at least two of the multiple arrays, to obtain post-processed outputs; and outputting at least one of said image-processed outputs resulting from said image processing and/or at least one of said post-processed outputs from said post-processing.

24. A non-transitory computer readable medium storing one or more sequences of instructions which, when said medium is accessed by one or more data processors including at least one hardware computing element, are executed by said one or more data processors, control a bifurcated data analysis process that extracts features from an image obtained from a plurality of arrays, said instructions comprising:

image processing parts of said image using said at least one hardware computing element, each part corresponding to a different one of said plurality of arrays, sequentially, to produce image-processed outputs that are different from said image and contain information extracted from said image;

post-processing said image-processed outputs corresponding to at least two of said plurality of arrays according to different post-processing protocols with respect to different ones of said parts of said image, in an automated batch process to produce post-processed outputs; and outputting at least one of said image-processed outputs and/or at least one of said post-processed outputs.

* * * * *